(12) United States Patent
Kassam-Adams et al.

(10) Patent No.: US 11,042,668 B1
(45) Date of Patent: Jun. 22, 2021

(54) SYSTEM FOR PREPARING DATA FOR EXPERT CERTIFICATION AND MONITORING DATA OVER TIME TO ENSURE COMPLIANCE WITH CERTIFIED BOUNDARY CONDITIONS

(71) Applicant: Datavant, Inc., San Francisco, CA (US)

(72) Inventors: Shahir Kassam-Adams, Lovingston, VA (US); Jason A. LaBonte, Natick, MA (US); Paul J. Bayless, Burke, VA (US)

(73) Assignee: Datavant, Inc., San Francisco, CA (US)

( * ) Notice: Subject to any disclaimer, the term of this patent is extended or adjusted under 35 U.S.C. 154(b) by 107 days.

(21) Appl. No.: 16/382,462

(22) Filed: Apr. 12, 2019

Related U.S. Application Data

(60) Provisional application No. 62/657,636, filed on Apr. 13, 2018, provisional application No. 62/656,915, filed on Apr. 12, 2018.

(51) Int. Cl.
*G06F 21/62* (2013.01)
*G16H 10/60* (2018.01)

(52) U.S. Cl.
CPC ......... *G06F 21/6254* (2013.01); *G16H 10/60* (2018.01)

(58) Field of Classification Search
CPC ..... G06F 21/6254; G16H 10/60; G16H 10/20
See application file for complete search history.

(56) References Cited

U.S. PATENT DOCUMENTS

| | | |
|---|---|---|
| 5,892,900 A | 4/1999 | Ginter et al. |
| 6,397,224 B1 | 5/2002 | Zubeldia et al. |
| 6,732,113 B1 | 5/2004 | Ober et al. |
| 6,734,886 B1 | 5/2004 | Hagan et al. |
| 6,804,787 B2 | 10/2004 | Dick |
| 7,120,928 B2 | 10/2006 | Sheth et al. |
| 7,269,578 B2 | 9/2007 | Sweeney |
| 7,376,677 B2 | 5/2008 | Ober et al. |
| 7,428,706 B2 | 9/2008 | Hagan et al. |

(Continued)

OTHER PUBLICATIONS

Final Office Action for U.S. Appl. No. 15/045,605, dated May 8, 2020.

(Continued)

*Primary Examiner* — Paul E Callahan
(74) *Attorney, Agent, or Firm* — Morse, Barnes-Brown & Pendleton, P.C.; Sean D. Detweiler, Esq.

(57) ABSTRACT

A method and apparatus for certifying the de-identification actions necessary to take on a data set to make it compliant with privacy and security regulations is streamlined and automated using the invention. Preparing the data for certification is greatly simplified and accelerated by the system, as is interaction with the certifier in the approval process. After certification, the invention allows for the continuous automatic monitoring of the data set to ensure that its profile does not shift over time such that the certified de-identification actions are no longer sufficient to ensure regulatory compliance, and can signal the user and/or certifier that a new certification process must be repeated. Alternatively, if no shift is detected, a user and/or certifier can agree that no new certification is needed.

21 Claims, 4 Drawing Sheets

(56) References Cited

U.S. PATENT DOCUMENTS

| | | | |
|---|---|---|---|
| 7,519,591 B2 | 4/2009 | Landi et al. | |
| 7,526,485 B2 | 4/2009 | Hagan et al. | |
| 7,543,149 B2 | 6/2009 | Ricciardi et al. | |
| 7,587,366 B2 | 9/2009 | Grim, III et al. | |
| 7,668,835 B2 | 2/2010 | Judd et al. | |
| 7,711,120 B2 | 5/2010 | Kimmel et al. | |
| 7,792,517 B2 | 9/2010 | Mowry et al. | |
| 7,827,234 B2 | 11/2010 | Eisenberger et al. | |
| 7,865,376 B2 | 1/2011 | Ober et al. | |
| 7,945,048 B2 | 5/2011 | Ricciardi et al. | |
| 8,024,339 B2 | 9/2011 | Barker et al. | |
| 8,037,052 B2 | 10/2011 | Kariathungal et al. | |
| 8,042,193 B1 | 10/2011 | Piliouras | |
| 8,069,053 B2 | 11/2011 | Gervais et al. | |
| 8,090,595 B2 | 1/2012 | Hartman | |
| 8,121,984 B2 | 2/2012 | Barbieri et al. | |
| 8,176,334 B2 | 5/2012 | Vainstein | |
| 8,275,850 B2 | 9/2012 | Kohan et al. | |
| 8,296,299 B2 | 10/2012 | Haskell et al. | |
| 8,296,341 B2 | 10/2012 | Hagan et al. | |
| 8,341,427 B2 | 12/2012 | Auradkar et al. | |
| 8,355,923 B2 | 1/2013 | Gervais et al. | |
| 8,364,969 B2 | 1/2013 | King | |
| 8,381,287 B2 | 2/2013 | Trotter | |
| 8,473,452 B1 | 6/2013 | Ober et al. | |
| 8,494,874 B2 | 7/2013 | Green, III et al. | |
| 8,560,456 B2 | 10/2013 | Williams | |
| 8,566,113 B2 | 10/2013 | Friedlander et al. | |
| 8,577,933 B2 | 11/2013 | Evenhaim | |
| 8,589,437 B1 | 11/2013 | Khomenko et al. | |
| 8,661,249 B2 | 2/2014 | Guarraci et al. | |
| 9,292,707 B1 | 3/2016 | Fontecchio | |
| 9,614,814 B2 | 4/2017 | Fontecchio | |
| 9,830,476 B2 | 11/2017 | Fontecchio | |
| 10,129,370 B2 * | 11/2018 | Levy | H04L 67/02 |
| 10,255,456 B2 | 4/2019 | Guglani et al. | |
| 10,713,390 B2 * | 7/2020 | Anderson | G06F 21/6245 |
| 2002/0073138 A1 | 6/2002 | Gilbert et al. | |
| 2002/0173971 A1 | 11/2002 | Stirpe et al. | |
| 2006/0053032 A1 | 3/2006 | Weiler et al. | |
| 2007/0162377 A1 | 7/2007 | Williams | |
| 2008/0147554 A1 | 6/2008 | Stevens et al. | |
| 2009/0106550 A1 | 4/2009 | Mohamed | |
| 2009/0287502 A1 | 11/2009 | Roberts et al. | |
| 2010/0042583 A1 | 2/2010 | Gervais et al. | |
| 2010/0070306 A1 | 3/2010 | Dvorak et al. | |
| 2010/0094758 A1 | 4/2010 | Chamberlain et al. | |
| 2010/0114607 A1 | 5/2010 | Kress et al. | |
| 2010/0205009 A1 | 8/2010 | Kostoff | |
| 2010/0211781 A1 | 8/2010 | Auradkar et al. | |
| 2010/0223467 A1 | 9/2010 | Dismore et al. | |
| 2010/0256994 A1 | 10/2010 | Eisenberger et al. | |
| 2011/0191245 A1 | 8/2011 | Ricciardi et al. | |
| 2012/0036360 A1 | 2/2012 | Bassu et al. | |
| 2012/0116800 A1 | 5/2012 | McCallie et al. | |
| 2012/0124637 A1 | 5/2012 | Dunaway | |
| 2012/0159637 A1 * | 6/2012 | Dove | G16H 10/60 726/26 |
| 2012/0204032 A1 | 8/2012 | Wilkins et al. | |
| 2012/0226916 A1 | 9/2012 | Hahn et al. | |
| 2012/0303558 A1 * | 11/2012 | Jaiswal | G06N 20/00 706/12 |
| 2012/0316898 A1 | 12/2012 | Levitt et al. | |
| 2013/0117126 A1 | 5/2013 | Coppinger | |
| 2013/0117128 A1 | 5/2013 | Coppinger | |
| 2013/0246097 A1 | 9/2013 | Kenney et al. | |
| 2013/0304504 A1 | 11/2013 | Powell | |
| 2013/0304542 A1 | 11/2013 | Powell | |
| 2013/0346104 A1 | 12/2013 | Pillai | |
| 2014/0013452 A1 | 1/2014 | Aissi et al. | |
| 2014/0040308 A1 | 2/2014 | Ober et al. | |
| 2014/0041047 A1 | 2/2014 | Jaye et al. | |
| 2014/0108049 A1 | 4/2014 | Fuhrmann et al. | |
| 2014/0108258 A1 | 4/2014 | Williams | |
| 2014/0122873 A1 | 5/2014 | Deutsch et al. | |
| 2015/0089357 A1 * | 3/2015 | Vandervort | G06F 40/166 715/256 |
| 2015/0095243 A1 | 4/2015 | Eiler et al. | |
| 2015/0095252 A1 | 4/2015 | Mattsson et al. | |
| 2015/0149208 A1 | 5/2015 | Lynch et al. | |
| 2016/0110648 A1 | 4/2016 | Baveja et al. | |
| 2016/0147945 A1 | 5/2016 | MacCarthy et al. | |
| 2016/0267238 A1 | 9/2016 | Nag | |
| 2016/0275309 A1 | 9/2016 | Austin et al. | |
| 2016/0344544 A1 | 11/2016 | Biesinger et al. | |
| 2017/0103179 A1 | 4/2017 | Jiao et al. | |
| 2017/0243028 A1 | 8/2017 | LaFever et al. | |

OTHER PUBLICATIONS

Http://mist-deid.sourceforge.net/ "MIST—The MITRE Identification Scrubber Toolkit".

Final Office Action from U.S. Appl. No. 15/045,605, dated Nov. 4, 2019.

Non-Final Office Actioon from U.S. Appl. No. 15/045,605, dated Feb. 13, 2020.

Non-Final Office Action U.S. Appl. No. 15/045,605, dated Jul. 18, 2019.

Non-Final Office Action from U.S. Appl. No. 16/135,972, dated Aug. 13, 2020.

Third Party Submission Under 37 CFR 1.290 for U.S. Appl. No. 15/045,605, made/submitted Mar. 29, 2019.

Notice of Allowance for U.S. Appl. No. 15/045,605, dated Oct. 14, 2020.

Non-Final Office Action for U.S. Appl. No. 16/382,447, dated Dec. 16, 2020.

Non-Final Office Action for U.S. Appl. No. 16/684,541, dated Feb. 18, 2021.

Notice of Allowance for U.S. Appl. No. 16/135,972, dated Jan. 28, 2021.

* cited by examiner

SYSTEM FOR PREPARING DATA FOR EXPERT CERTIFICATION AND MONITORING DATA OVER TIME TO ENSURE COMPLIANCE WITH CERTIFIED BOUNDARY CONDITIONS

CROSS-REFERENCE TO RELATED APPLICATION(S)

This application claims priority to U.S. Provisional Application No. 62/656,915, filed Apr. 12, 2018, and also claims priority to U.S. Provisional Application 62/657,636 filed Apr. 13, 2018. The disclosures of said applications are hereby incorporated herein by reference in their entirety. This application is also related to U.S. application Ser. No. 15/045,605, filed Feb. 17, 2016, now U.S. Pat. No. 10,910,089, issued Feb. 2, 2021. The disclosure of said application is hereby incorporated by reference in its entirety.

FIELD OF THE INVENTION

The present invention relates to mapping and profiling a data set to allow a certifier to determine the proper de-identification rules for compliance with regulations, and to monitor that data set over time to ensure continued compliance, and more specifically to providing a system for automatically mapping the elements of a data set to identify fields with sensitive information, suggesting the proper de-identification action to be taken on that field to make it compliant with regulations, allowing a certifier to view that information to approve or modify the de-identification actions, allowing the certifier to view a statistical profile of the data and a data sample, recording the certified de-identification actions and the certified data profile, and periodically comparing the profile of the data against the certified data profile to ensure that the data set has not drifted out of compliance.

BACKGROUND

Generally, conventional healthcare data systems are limited in their ability to access and share data sets containing sensitive and identifiable information to perform valuable types of analysis or research. The primary reason is the fact that this data contains regulated information such as protected health information ("PHI") or personally identifiable information (PII) (e.g., names, addresses, dates of birth, dates of death, social security numbers, etc.). Compliance with a great number of statutes, laws (e.g. federal and state privacy laws), regulations, rules, guidelines and best practices restricts how data containing such information may be processed, stored or transmitted. The Health Insurance Portability and Accountability Act (HIPAA) in particular restricts the ability to share protected health information unless the information is adequately de-identified using one of two approved methodologies. Consequently, it would be a violation to incorporate PHI elements into a healthcare data set to be used outside of the clinical context in which those elements were first collected if the information is not appropriately de-identified beforehand. An effective method for de-identifying health data sets is the expert determination method, which requires a statistical "expert" to evaluate the de-identified data and certify that the risk of re-identification of an individual represented in the data is "very small." Conventional systems, devices, and methods for this kind of compliance preparation require users to perform manual analysis and packaging of data sets (including data schemas or dictionaries, customized sets of statistics about the data, de-identified data samples, etc.) for an expert to review for regulatory adequacy, compliance and formal certification. The certifier must engage each new client by repeating this process, with lengthy times to educate each new user on the steps required, how to perform those steps, etc. Because of the time and effort involved, once the certifier has approved the proper set of de-identification actions that need to be performed on a data set, this process is not repeated for another 1+ years, during which time, the data set may have shifted substantially.

SUMMARY

There is a need for an automated and streamlined process that consistently prepares a data set for certification, offers risk threshold calculations and de-identification protocol recommendations, provides workflow tools for the certifier to interact with the data owner, records the final certified de-identification actions and accompanying data profile, and thereafter routinely and consistently compares the data sets profile against the certified profile to determine if the data has shifted to the extent that the certified rules are no longer sufficiently compliant. There is a need for improvements for enabling healthcare data sets within healthcare records to be accessible and useable without exposing protected healthcare information of the individual, which can be continually monitored and improved to prevent lapses in compliance on a continuous rather than periodic or ad hoc basis. The present invention is directed toward further solutions to address this need, in addition to having other desirable characteristics. Specifically, the process of certifying the de-identification actions necessary to take on a data set to make it compliant with privacy and security regulations is streamlined and automated using the invention. Preparing the data for certification is greatly simplified and accelerated by the system, as is interaction with the certifier in the approval process. After certification, the invention allows for the continuous automatic monitoring of the data set to 1) ensure that its profile does not shift over time and compromise the adequacy of the de-identification, and 2) signal to the user and/or certifier that a new certification process must be repeated.

In accordance with example embodiments of the present invention, a system for managing compliance with certified boundary conditions comprises a centralized management platform, comprising a processor, a pre-certification data map with de-identification rules, one or more databases and memory, configured to communicate data to and from a user device over a telecommunications network; an automapping module configured to map each field of a data set of the user device to standard field names, identify sensitive information and suggest de-identification actions to anonymize values in each field in a manner compliant with regulations, and transfer to the centralized management platform a centrally stored data map; a configuration tool configured to designate a sample record set size and modify the de-identification rules to be applied to fields in the data set of the user device when a user runs locally installed software to de-identify the data set; a certification approval module configured to mark de-identification rules stored in the configuration tool as the certified rules and designate conditions or boundary ranges; a monitoring data profile module configured to create baseline monitoring data files from the data set and comparator monitoring data files from a de-identified data set after the user runs the locally installed software to apply the certified rules to the data set; and a comparison module configured to compare attributes between comparator monitoring data files and baseline monitoring data files, and send an alert when any field deviates beyond designated conditions or boundary ranges.

In accordance with aspects of the present invention, the system can further comprise a data converter module locally installed and configured to convert data in a database structure into a flat file format to create a flat file output for each table in a database of the data set, retaining field names and formats output to data files comprising the baseline monitoring data files, wherein the flat file output or outside sources can serve as an input to the automapping module and serve as the baseline monitoring file. The data converter module also can enable the user to designate one or more databases that the data converter module processes.

In accordance with aspects of the present invention, the centralized management platform can comprise an invitation module that enables the user to invite a certifier to register to access files the user transmits to the centralized management platform, wherein registering, using a register module, further comprises: registering one or more certifier and certifier software; assigning one or more unique encryption keys and permissions to each of the one or more certifier and certifier software; identifying parameters and requirements for certifier software; generating configuration files for certifier and certifier software; providing the unique encryption keys and configuration files to the certifier and certifier software at one or more certifier devices; and authenticating each certifier access using the permissions and the one or more unique encryption keys with the register module, wherein the transmitting is further based on authenticating using the permissions and the one or more unique encryption keys.

In accordance with aspects of the present invention, the sensitive information in the data set can comprise protected personally identifiable information (PII) or protected health information (PHI) and wherein a record set request derived from configuration tool input comprises a requested number of records based on the sample record set size. The sensitive information in the data set further can comprise one or more of social security numbers, credit card numbers, financial account information including financial account numbers, names including maiden names, birth dates, death dates, passport numbers, license numbers, certificate numbers, taxpayer identification numbers, patient identification numbers including medical record numbers, health plan beneficiary numbers, telephone numbers, fax numbers, personal identification numbers, title numbers, serial numbers, personal characteristic data including images, biometric identifying data, specific geographic identifiers, zip codes, personal addresses, street addresses, mailing addresses, email address information, uniform resource locator (URL), media access control (MAC) addresses, and internet protocol (IP) addresses, as well as other known types of PII and PHI including HIPAA identifiers codified by 45 C.F.R. § 164 or readily apparent to those of skill in the art.

In accordance with aspects of the present invention, the automapping module can be configured to identify and manage sensitive information in the data set of the user by parsing and processing each field in a flat file created from the data set, to identify a type of data contained in each field, a field name, and values in each field to map each field to a list of standard field names; analyzing a data format of the values in each field then matching, based on the data format of the values, elements of each field being analyzed against standard elements and assigning a suggested standard field name that is a match to map each field of a data set of the user to standard field names, and assigning a flag designating each field containing sensitive information values as personally identifiable information (PII) or protected health information (PHI), as well as assigning one or more suggested de-identification actions to anonymize the values in each field in a manner compliant with regulations, and automatically validating the type of data contained in each field. The automapping module can output a data layout comprising assigned suggested standard field names, flags designating each field as personally identifiable information (PII) or protected health information (PHI), and assigned suggested de-identification actions for each field, and the automapping module enables the user to validate identified field types, modify, or add to the information in output data layouts, and to transfer a final data map from the automapping module to the centralized management platform to create a centrally stored data map. The automapping module can assign a standard field name associated with a specific data format and specific values comprising the specific data format. The automapping module can assign a standard field name comprising a "name," a specific data format comprising text, and specific values in the specific data format comprising a list of actual names.

In accordance with aspects of the present invention, the one or more de-identification actions to anonymize the values can comprise removing the values and sensitive information from each field of the data set to create a de-identified data set comprising data fields that are blank or nulled, and adding one or more unique encrypted tokens, each comprising a randomized character string, to each de-identified record of the de-identified data set, making each de-identified record of the data set unique to a particular individual but without the sensitive information and sensitive data values used to create each de-identified and tokenized record.

In accordance with aspects of the present invention, the configuration tool can be configured to designate a sample record set size for data to be received for analysis at the centralized management platform and wherein the configuration tool is configured to enable the certifier to modify the centrally stored data map to modify the de-identification rules to be applied to fields in the user's data set when the user runs locally installed software to de-identify the data set.

In accordance with aspects of the present invention, the system can further comprise a statistical data profile module configured to process the de-identified data set created after the user runs locally installed software to de-identify the data set, creating output data tables to determine effectiveness of de-identification wherein each field is analyzed to create metrics for each field type, which are then transmitted to the centralized management platform. The statistical data profile module can be configured to analyze each field and create metric for each field type comprising one or more metric selected from the group consisting of average, mode, median, sample size, fill rate, outliers, and combinations thereof, enabling the user to transmit the output data tables from the statistical data profile module to the centralized management platform, and wherein the statistical data profile module and the system can be further configured to perform real-time calculations for metrics comprising k-anonymity or frequency indicating, based on a set level comprising a threshold for a certification standard for anonymity, whether the data meets certification requirements, wherein the metrics are included in the alert and in a reporting log stored in a database of the central management platform. A sample data creation module can be configured to select a requested number of records from the de-identified data files to match the sample record set size designated by the configuration tool and transmit the sample data created to the centralized management platform, wherein the sample data are ingested and stored by a data profile and a sample storage module configured to enable the certifier to retrieve files from for review and analysis In accordance with aspects of the present invention, the certification approval module can be configured to enable the certifier to mark rules stored in the configuration tool as the approved or certified rules and designate conditions or boundary ranges for individual fields in an approved data profile, and wherein the user runs the locally installed software to apply the certified rules from the certification approval module to de-identify the data set. The monitoring data profile module can be configured to create a baseline monitoring data profile comprising baseline monitoring data files from the data set and a comparator monitoring data profile comprising comparator monitoring data files from a de-identified data set processed from a most current version of the data set after the user runs the locally installed software to apply the certified rules, then transmits the baseline monitoring data profile comprising the baseline monitoring data files from the data set and the comparator monitoring data profile comprising comparator monitoring data files to the central monitoring platform. The comparison module also can be further configured to store a baseline monitoring data profile and a comparator monitoring data profile within the central management platform to compare attributes of each field between comparator monitoring data files and baseline monitoring data files, to determine a degree of difference, then check the degree of difference in each field against the designated conditions or boundary ranges corresponding to each field set by the certifier using the certification approval module, and send an alert to the certifier and/or user when any field deviates by more than a set level that is beyond designated conditions or boundary ranges, recording a result in a reporting log stored in a database of the central management platform. The alert and the reporting log can further comprise metrics and an identification of any fields or values that require modification to allow the set level comprising a threshold for a certification standard for anonymity, to be met or surpassed.

In accordance with aspects of the present invention, the system can comprise a plurality of user devices, the centralized management platform comprises a plurality of processors, one or more pre-certification data maps with de-identification rules, one or more databases and memory, configured to communicate data to and from the plurality of user devices over a telecommunications network. One or more automapping modules can be configured to map each field of one or more data sets of the plurality of user devices to standard field names, identify sensitive information and suggest de-identification actions to anonymize values in each field in a manner compliant with regulations, and transfer to the centralized management platform one or more centrally stored data maps. The configuration tool can be configured to designate a sample record set size and modify the de-identification rules to be applied to fields in the one or more data sets of the plurality of user devices when one or more users run locally installed software to de-identify the one or more data sets, and one or more monitoring data profile modules can be configured to create baseline monitoring data files from the one or more data sets and comparator monitoring data files from one or more de-identified data sets after the one or more users run the locally installed software to apply the certified rules to the one or more data sets.

In accordance with example embodiments of the present invention, a method for managing compliance with certified boundary conditions comprises: receiving, a at centralized management platform comprising a processor, a pre-certification data map with de-identification rules, one or more databases, and memory, a data set from a user device configured to communicate over a telecommunications network; analyzing, using an automapping module, values in each field of the data set, mapping each field to standard field names, identifying sensitive information and suggesting de-identification actions compliant with regulations, then transferring a centrally stored data map to the centralized management platform; modifying, using a configuration tool, the de-identification rules to be applied to fields in the user's data set when the user runs locally installed software to de-identify the data set; determining, using a statistical data profile module, effectiveness of de-identification and creating metrics for each field type then transmitting output data tables to the centralized management platform; marking, using a certification approval module, rules stored in the configuration tool as the approved or certified rules, and designating conditions or boundary ranges; creating, using a monitoring data profile module, a baseline monitoring data profile from the data set and a comparator monitoring data profile from a de-identified data set after the user runs the locally installed software to apply the certified rules; and comparing, using a comparison module, attributes between comparator monitoring data files and baseline monitoring data files, and sending an alert when any field deviates beyond designated conditions or boundary ranges.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
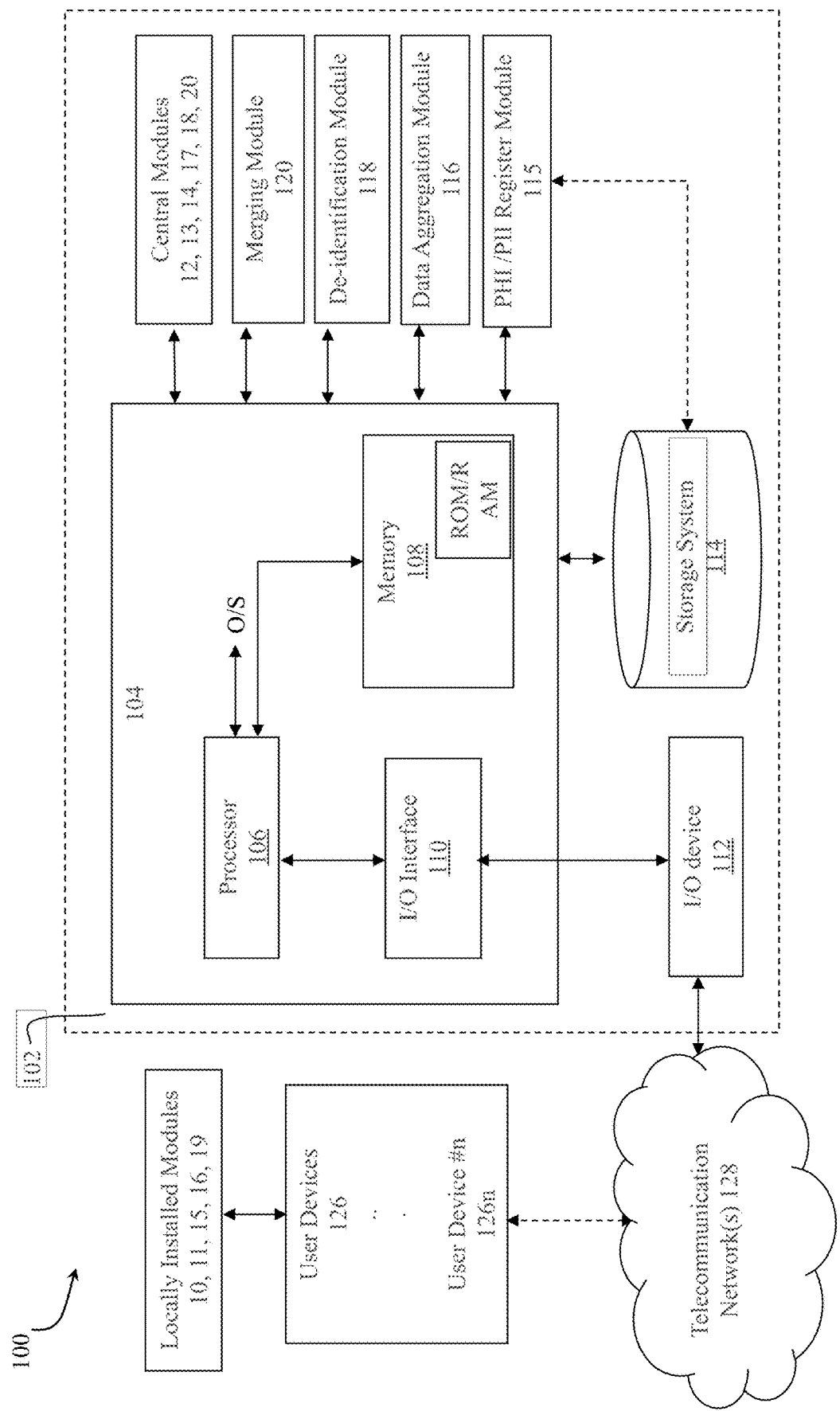
FIG. 1 is a flow diagram depicting the workflow of the certification process in accordance with one embodiment.

An illustrative embodiment of the present invention relates to certifying the de-identification actions necessary to take on a data set to make it compliant with privacy and security regulations, which is streamlined and automated using the invention. Preparing the data for certification is greatly simplified and accelerated by the system, as is interaction with the certifier in the approval process. After certification, the invention allows for the continuous automatic monitoring of the data set to ensure that its profile does not shift over time such that the certified de-identification actions are no longer sufficient to ensure regulatory compliance, and can signal the user and/or certifier that a new certification process must be repeated. Alternatively, if no shift is detected, a user and/or certifier can agree that no new certification is needed.

An illustrative embodiment of the present invention relates to a specific system and method with means that improves the existing technology by reciting specific structures, functions and steps that accomplish the desired result through an inventive arrangement by combining de-identified data, tokenized data and rules for creating anonymity in data with healthcare data in a manner that does not violate HIPAA or other privacy related regulations that restrict PHI or PII. In particular, data is aggregated from different sources (e.g., health care records, data stores) or obtained by one or more instances of software deployed on one or more client devices, then the healthcare data is analyzed to determine data types, data formats, fields and values by matching to elements of existing data sets, a set of de-identification rules dictating and instantiating de-identification actions is implemented to transform the relevant data into de-identified data by removing or modifying all elements regarded as protected health information or personally-identifiable information (also known as personally identifying information), and a unique encrypted person token is added to each record. The "tokenized" data may be merged with other healthcare or personal data sets that have been de-identified and tokenized in a similar process, that uses a combined order of specific incorporated rules and functions, not mere use of the computer and existing data processing technology, thereby improving the existing data management technological processes that renders health care information or encrypted information into a specific format that is then used and applied to create desired results of data sets, that can be used together in an encrypted and privacy preserving manner and can be monitored by a certifier. This represents an additional improvement in the technology where prior data sets could not be continually evaluated for compliance by comparison between baseline monitoring and comparator data sets to track trends and deviations. In accordance with aspects of the present invention, computing hardware devices are tied to the system and the method steps, such that the present invention involves multiple transformation steps necessarily tied to the computing hardware devices. Additionally, the transformation steps performed in the present invention are designed to provide an improvement necessitated by changes in technology (e.g., multiple instances of the same encryption software and duplicated health care records, and the presence of large data sets that make conventional certification processes too slow to be feasible or easily modified) and that the present invention solves the problem created by these changes in technology. Accordingly, the present invention is also an improvement to the technical area of software configuration and encryption management. Advantageously, the process of the present invention can further yield data that can be aggregated and analyzed for the purposes of both measuring compliance with regulations and substantive valuable research, which conventional systems lack. Specifically, the healthcare data sets are merged with other data including existing personal data records by matching techniques that allow the system to use historic information to properly identify procedures for de-identifying data in compliance with regulations without resorting to manual evaluation and without exposing any sensitive information, while improving the system as more data sets are processed. Using the system and method of the present invention provides a specific, non-abstract improvement to computer functionality that enables "individuals" (e.g., de-identified healthcare records) in a healthcare data set to be marked, tracked, and evaluated for privacy and other compliance consistently and persistently without exposing protected health information, personally-identifiable information or other personal data. This in turn enables databases or data structures containing health care data sets, operated by separate, potentially unrelated entities, to query, receive, and incorporate (including by merging) data sets including personal data in a separate database or data structure that ordinarily would not be capable of interacting due to the above discussed restrictions on combining such data and the existing technological requirements of reproducing data within data structures in order to preserve unique identifiers and data used to accurately correlate or match data based on association with an underlying entity. This represents a practical application of a centralized encryption management platform 102 that enables databases or data structures containing health care data sets, operated by separate, potentially unrelated entities, to query, receive, and incorporate (including by merging) data sets while the parties are using the centralized encryption management platform 102, including related data in a separate database or data structure that ordinarily would not be capable of interacting due to the above discussed restrictions on combining such data and the existing technological requirements of reproducing data within data structures in order to preserve unique identifiers, encryption, and data used to accurately correlate or match data based on association with an underlying entity. The data sets created by the present invention, contain the de-identified unique encrypted person tokens, an indicator of the individual previously identified in the data record, and personal data record data that is encrypted by the centralized encryption management platform 102 unique encryption key and the configuration file to each of the one or more registered instances of software deployed on one or more user devices that is stored using the secure data storage module and storage device. The present invention dramatically increases the capabilities of entities to comply with federal and state privacy laws. In particular, the present invention allows for controlled sharing of disparate data. Accordingly, the process carried out in the present invention produces a consistent, repeatable and certifiably compliant method of protecting personal information, when sharing data, while still maintaining the rights of data sources to protect their data. This transformed data functions differently than, and achieves benefits over, conventional database structures and data therein, providing increased flexibility, and the ability to combine otherwise un-combinable data sets. To improve accuracy without sacrificing privacy compliance and data security, the data sets provide that the encrypted person token is unique to a particular individual. For example, the present invention determines how many John Doe's share the same birthday and live in the same city/state. If there are two John Does sharing the same birthday, residence, etc. and a data record indicates there is a John Doe matching that information, the system can merge the records with a unique encrypted person token, but if the records indicate similarity but the existence of two distinct John Does, the system can then assign a unique encrypted person token to the two distinct John Does, preserving the distinction even when subsequent data sets only contain record information that is common to both John Does. Once the data sets and healthcare data sets are merged, a user can perform analysis of anonymous healthcare data. This functionality provides many added benefits not previously available to healthcare practitioners. For example, data is critical to properly understand the effectiveness and safety of clinical treatment. Marking status for de-identified patients in healthcare data is critical. As would be appreciated by one skilled in the art, the personal data sets are not limited to individuals on file but can also be extended to individuals e.g. associated with a particular disease without departing from the scope of the present invention. The de-identification of healthcare data sets and data sets provided by the present invention enables indicators to be merge-able with the healthcare data sets in such a way that data sets from disparate sources but relating to a same individual can be matched up and associated with each other without the exposure of PHI.

FIG. 1 through FIG. 4, wherein like parts are designated by like reference numerals throughout, illustrate an example embodiment or embodiments for managing certification and compliance with certified boundary conditions to improve the functionality of data de-identification in encrypted data sets, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

FIG. 1 illustrates an example embodiment or embodiments for the certification of encrypted data, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The present invention relates to a system of locally installed software (the Software) and a central platform (Platform). The Software acts upon data stored locally where the Software is installed, and communicates with the Platform to send and receive information necessary for the operation of the system. Users interact with the Software locally to perform some actions, and interact with the Platform to perform others. Specifically, FIG. 1 depicts a computing system 100 including at least a centralized encryption management platform 102 including a computing device 104 having a processor 106, a memory 108, a storage system or device 114, and an input/output interface 110. The system 100 may also include one or more input/output devices 112. The centralized encryption management platform 102, including the computing device 104, may be a general purpose computer that is specialized using software or a specialized computer system. For example, the computing device 104 may include a single computing device, a collection of computing devices in a network computing system, a cloud computing infrastructure, or a combination thereof, as would be appreciated by those of skill in the art. In accordance with example embodiments, the computing device 104 may be a server system in communication with a database (e.g., storage device 114). Similarly, as would be appreciated to one of skill in the art, the storage device 114 may include any combination of computing devices configured to store and organize a collection of data. For example, the storage device 114 may be a local storage device on the computing device 104, a database storage component of the centralized encryption management platform 102, a remote database facility, or a cloud computing storage environment functioning as a data store. The storage device 114 may also include a database management system utilizing a given database model configured to interact with a user for analyzing the database data.

The computing system 100 of FIG. 1 may further include one or more client computing devices 126 . . . 126n each executing client software. Similar to the computing device 104, the client computing devices 126 may each include a single computing device, a collection of computing devices in a network computing system, a cloud computing infrastructure, or a combination thereof, as would be appreciated by those of skill in the art. Additionally, the client computing devices 126 may each include or otherwise be in communication with storage device(s). As would be appreciated by one skilled in the art, the storage device(s) may be similar to the storage device 114 in architecture and implementation. In accordance with example embodiments of the present invention, the plurality of client computing devices 126 may be de-centralized devices located remotely from the centralized encryption management platform 102. For example, each of the plurality of client computing devices 126 may be independent institutions, organizations, and businesses, each collecting and storing a variety of personal data records. The functionality of the present invention is provided by the hardware of FIG. 1 through the execution of software that makes the hardware perform in the desired manner. In practice in the system 100, the one or more user devices 126 . . . 126n are configured to communicate data to and from the one or more computing devices 104 comprising one or more processors 106, memory 108, an interface 110, one or more input-output devices 112 over one or more telecommunications networks 128, where data may be stored in one or more databases or data storage device 114 comprising at least previously de-identified healthcare data sets with encrypted person tokens and comprising lookup lists stored therein. The system 100 also includes a set of modules, which may be implemented locally or remotely as a set of hardware or software instances, and used by the one or more computing devices 104 to perform tasks for the system 100. A data aggregation module 116 is configured to aggregate data records with protected health information included therein from a plurality of data sources. A merging module 120 is configured to transform all of the data records associated with identifiable individuals into data sets, each of the data sets uniquely associated with each of the identifiable individuals. A register module 115 is used for managing clients and personal healthcare information and personally-identifiable information (also known as personal identifying information). A de-identification module 118 is configured to: remove the protected health information from the data sets to create de-identified data sets 136; create an encrypted person token based on the removed protected health information, wherein the encrypted person token is uniquely associated with an individual previously associated with the removed protected health information. The merging module 120 is further configured to merge the de-identified data sets with de-identified healthcare data sets based on matching encrypted person tokens associated therewith; and wherein resulting merged data sets include data records and a stored in a location segregated from protected health information and personal identification information, wherein delivering of records associated with identifiable individuals is prevented.

The plurality of certifier, user, or client computing devices 126 . . . 126n are made functional in the system 100 by registering one or more clients and software. During registration the system 100 assigns one or more unique encryption keys and permissions to each of the one or more clients and client software, then identifies parameters and requirements for client and client software that will be needed to achieve the clients' data processing and data handling capabilities and goals. The system 100 then generates configuration files for client and client software to be implemented or downloaded onto the one or more client devices or user devices that are based on the underlying parameters and requirements for client and client software derived from client characteristics. Then the system 100 provides the one or more unique encryption keys and one or more configuration files to the client and client software using one or more telecommunications network connections or other transmission means known by those of ordinary skill in the art.

Figure 2:
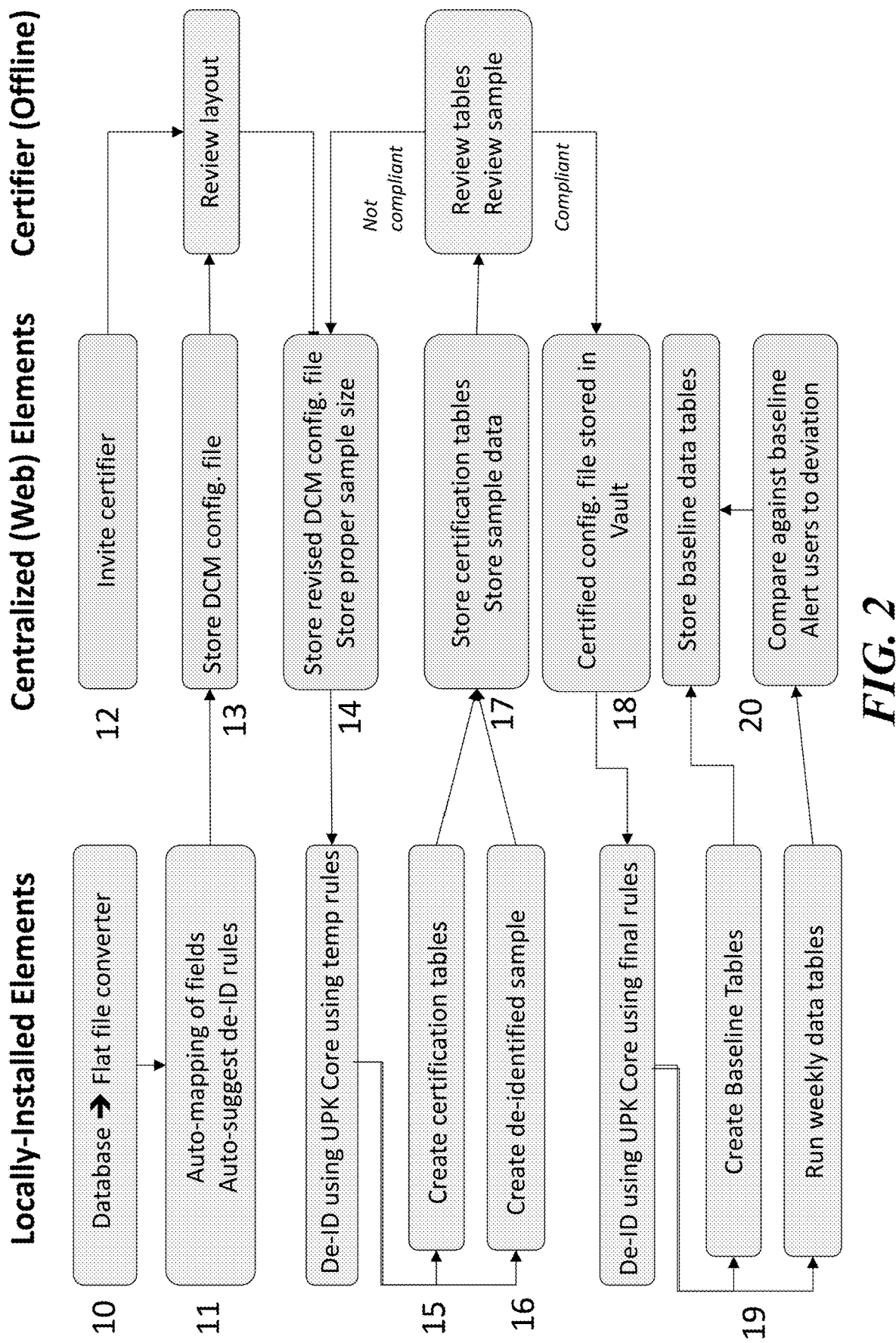
FIG. 2 is a flow diagram depicting the workflow of the certification process in accordance with one embodiment.

FIG. 2 is a flow diagram depicting the workflow of the certification process in accordance with one embodiment. The system includes a locally installed software module 10 to convert data in a database structure to a flat file format. The user designates the database that the data converter module 10 should process. The data converter module 10 creates a flat file output for each table in the database, retaining the field names and formats in the output files.

The flat files from the data converter module 10, or from another source, serve as the input to an automapping module 11. The automapping module 11 processes each field in the flat file to identify the type of data contained in the field. The automapping module 11 analyzes the data format of the values in the field, the field name, and the values themselves to attempt to map the field to a list of standard field names. Each standard field name (e.g. First Name) is associated with a specific data format (e.g. text) and specific values (e.g. a list of actual first names). The automapping module 11 matches the elements of the field being analyzed against these associated elements and suggests the closest matching standard field name. Each standard field name is also associated with a flag designating the field as personally identifiable information (PII) or protected health information (PHI) (where these terms are sometimes referred to as personal identification information, personal health information, electronic protected health information, individually identifiable information, etc. and so these terms include such equivalent terms), as well as the suggested de-identification action (e.g. removal) that should be taken to anonymize the values in that field in a manner compliant with regulations. As used in this application, personally identifiable information (PII) and protected health information (PHI) are defined by the definitions provided by and codified in 45 C.F.R. § 164, including the HIPAA identifiers recited therein or readily apparent to those of skill in the art, and currently may refer to, for example, one or more of social security numbers, credit card numbers, financial account information including financial account numbers, names including maiden names, birth dates, death dates, passport numbers, license numbers, certificate numbers, taxpayer identification numbers, patient identification numbers including medical record numbers, health plan beneficiary numbers, telephone numbers, fax numbers, personal identification numbers, title numbers, serial numbers, personal characteristic data including images, biometric identifying data, specific geographic identifiers, zip codes, personal addresses, street addresses, mailing addresses, email address information, uniform resource locator (URL), media access control (MAC) addresses, and internet protocol (IP) addresses. The output of the automapping module 11 is a data layout containing the suggested standard field names, PII or PHI flags, and suggested de-identification actions for each. The user has the ability to validate, modify, or add to the information in this output to create a final map.

The Platform contains an invitation module 12 that allows the user to invite a certifier to register and/or login to the Platform to access the files the user will place in the Platform.

The user can upload or otherwise transfer the final map from the automapping module 11 to the Platform to create a centrally stored data map 13. This final map is same or similar in format to the method described in U.S. Provisional Application entitled "METHODS AND SYSTEMS PROVIDING CENTRAL MANAGEMENT OF DISTRIBUTED DE-IDENTIFICATION AND TOKENIZATION SOFTWARE FOR SHARING DATA" (U.S. Provisional Application No. 62/656,915, filed on Apr. 12, 2018, and herein referred to as Vault reference, which is incorporated herein by reference) and the ingestion and storage of the information to create a data processing map is also the same or similar to the method described in the Vault reference. The certifier invited through the invitation module 12 is allowed to view and/or download the centrally stored data map 13 for review.

After review, the certifier can modify the centrally stored data map using an offline or online configuration tool 14 in the same or similar method as described in the Vault reference. The configuration tool 14 allows the certifier to modify the de-identification actions (rules) to be applied to the fields in the user's data set. The configuration tool 14 also allows the certifier to designate the size of the sample record set they would like to receive for analysis. When the certifier has completed their use of the configuration tool 14, the Platform sends an alert to the user.

Upon alert, the user runs the locally installed Software to de-identify the data set using the methods described in the Vault reference. The de-identified data is then processed by a statistical data profile module 15 to create the data tables necessary to determine the effectiveness of de-identification. Using the standard field names added by the automapping module 11, the statistical data profile module 15 analyzes each field and creates metrics such as average, mode, median, sample size, fill rate, outliers, etc. as relevant to each field type, or calculates metrics including k-anonymity or frequency. The user uploads or otherwise transmits the output data tables from the statistical data profile module 15 to the Platform.

The de-identified data is also processed by a sample data creation module 16. Using the sample size designated by the certifier in configuration tool 5, the sample data creation module 16 selects the requested number of records from the de-identified data file(s) to match the requested sample size. The user uploads or otherwise transmits the sample data created by the sample data creation module 16 to the Platform.

The transmitted outputs from the statistical data profile module 15 and the sample data creation module 16 are ingested and stored by the data profile and sample storage module 17. Upon ingestion, the data profile and sample storage module 17 can alert the certifier that the files are ready for review. The certifier can view and/or download the files from the data profile and sample storage module 17 to review and perform any other analysis they desire. If the certifier does not believe the de-identification rules or sample size stored by the configuration tool 14 are appropriate, they can use the configuration tool 14 to modify any de-identification rule, triggering a repetition of modules 15-17.

If the certifier considers the de-identification rules to be sufficient, they can use a certification approval module 18 to mark the rules stored in the configuration tool as the approved or certified rules. The certifier can also use the certification approval module 18 to designate conditions or boundary ranges for individual fields in the approved data profile. The certifier is also able to attach a certification report to the approved or certified rules. Upon completion of the certifier's work, the certification approval module 18 alerts the user that certification is complete.

Upon alert from the certification approval module 18, the user runs the local software to apply the certified rules from the certification approval module 18 to de-identify their data set. The monitoring data profile module 19 creates a baseline monitoring data profile from the data set when it is first run. The user can upload or otherwise transmit the baseline monitoring data profile to the Platform.

Thereafter, at periods (e.g. weekly, monthly, etc.) designated by the user, de-identified data from the most current version of the data set is processed by the monitoring data profile module 19 to create a comparator monitoring data profile. The user can upload or otherwise transmit the comparator monitoring data profile to the Platform.

The baseline monitoring data profile is stored in a comparison module 20 in the Platform. Comparator monitoring data profiles are also stored in the comparison module 20. The comparison module 20 compares the attributes of each field between the comparator and baseline monitoring data files to determine the degree of difference. The comparison module 20 checks the degree of difference in each field against the allowed conditions or boundary ranges for that field that was set by the certifier in the certification approval module 18. If any field deviates by a level that is beyond the allowed condition or boundary range, the comparison module 20 sends an alert to the user and/or certifier to that effect. All findings from each instance in which the comparison module 20 runs to assess the deviation from the latest comparator monitoring data profile against the baseline monitoring data profile is recorded in a reporting log maintained by the comparison module 20. Users can view or export the elements in the reporting log as they wish.

As can be seen from the above description, the present invention provides an automated mapping tool that identifies personally-identifiable information (PII) in the user's data set, allows users to validate the identified field types, and then automatically suggests the appropriate de-identification action to take on that field.

The present invention also provides a central system that hosts a pre-certification data map with de-identification rules for a certifier to view or download, and that allows the certifier to modify the de-identification rules to be used.

The present invention also provides an automated system for generating a de-identified sample data set using the de-identification rules and sample size configured by the certifier, and automatically creating a statistical data profile.

The present invention also provides a central system that hosts the de-identified sample data and the statistical data profile for viewing or downloading by the certifier.

The present invention also provides a central system through which the certifier can "approve", lock, or otherwise record that the de-identification actions to be taken are appropriate for the data set, and can attach a certification report to this rule set as desired.

The present invention also provides a central system through which the certifier can designate a data profile as belonging to the approved de-identification actions, which can act as the comparator or "baseline" data profile for future monitoring of data set shifts. Further, the certifier can designate the boundary ranges or conditions that are allowed for future data profiles without the de-identification actions being rendered non-compliant.

The present invention also provides an automated system that can be configured to periodically create a statistical data profile of the data set on an ongoing basis, compare it to the baseline data profile, and alert the user and/or certifier if any element has shifted beyond an allowed boundary condition.

The present invention thus provides a faster, simpler, and more standard certification process for data owners.

The present invention also provides continuous monitoring for shifts in data sets to ensure that certified de-identification actions are still allowing compliance with regulations.

The present invention also provides the ability to delay or accelerate new certifications based on how fast the data set is drifting.

Figure 3:
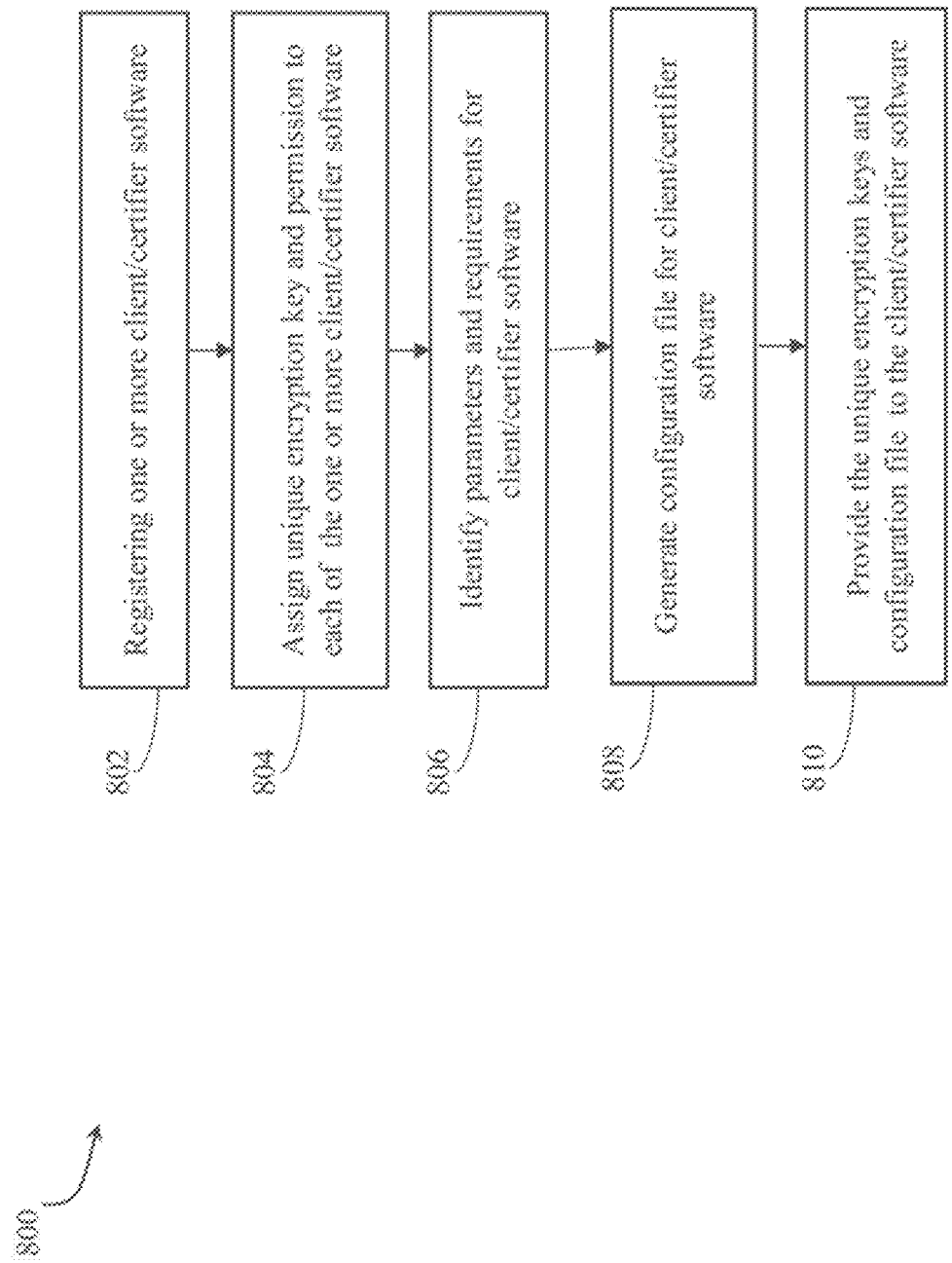
FIG. 3 is a flow diagram depicting the workflow of the certification process in accordance with one embodiment.

FIG. 3 depicts an exemplary flow chart 800 showing the implementation and operation of the processes of the present invention. In particular, process 800 depicts the operation of the centralized encryption management platform 102 managing data for the one or more instances of distributed client software to facilitate the updated data encryption for data stored on each of the plurality of client computing devices 126. At step 802, the simulation system 100 registers one or more clients on or more instances of client software deployed on one or more client computing devices 126, as discussed with respect to FIG. 1-FIG. 2. In certain embodiments, registration involves adding or otherwise modifying data associated with a site or software instance. At step 804, the system 100 assigns one or more unique encryption keys and permissions to each of the one or more registered client software instances on each certifier or client computing device 126 interacting with the centralized encryption management platform 102 computing device 104. In certain embodiments, the permissions are indicated by a license file generated in response to configured user and permission data for the respective software instance. In some embodiments, the unique encryption key and permission or license file are stored in a storage device 114 configured as a secure data storage. At step 806, the centralized encryption management platform 102 identifies the parameters and requirements associated with the registered software instance on each certifier or client computing device 126. At step 808, the system 100 generates one or more configuration files for each instance of the client software deployed on each client computing devices 126, as discussed with respect to FIG. 1-FIG. 2. In accordance with example embodiments of the present invention, the configuration files are generated from a data processing map which in turn was generated based on de-identification rules, token creation rules, field names and data layouts specified for the particular instance of client software on the certifier or client computing device 126, as well as input including client parameters such as requested number of records, and requested set of fields. In some embodiments, the configuration file is stored in a storage device 114 configured as a secure data storage. At step 810, the system 100 provides the one or more unique encryption keys and the one or more configuration files to the appropriate client software instance deployed on a certifier or client computing device 126. In certain embodiments, the system 100 further provides additional data, such as non-configurable private data like master hash seeds/salts.

Figure 4:
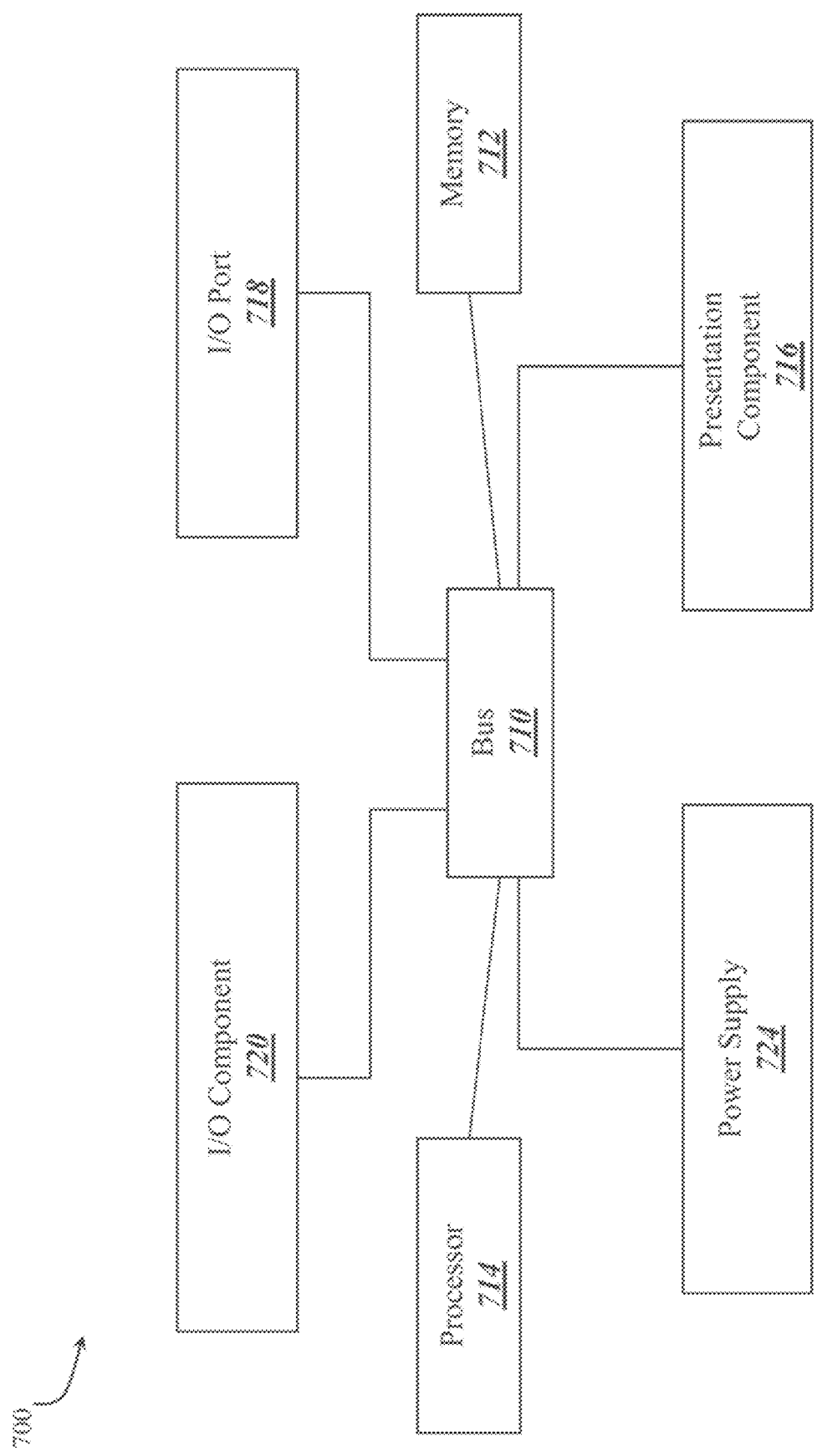
FIG. 4 is a flow diagram depicting the workflow of the certification process in accordance with one embodiment.

Any suitable computing device can be used to implement the client computing devices 126 . . . 126*n* and methods/functionality described herein. One illustrative example of such a computing device 700 is depicted in FIG. 4. The computing device 700 is merely an illustrative example of a suitable computing environment and in no way limits the scope of the present invention. A "computing device," as represented by FIG. 4, can include a "workstation," a "server," a "laptop," a "desktop," a "hand-held device," a "mobile device," a "tablet computer," or other computing devices, as would be understood by those of skill in the art. Given that the computing device 700 is depicted for illustrative purposes, embodiments of the present invention may utilize any number of computing devices 700 in any number of different ways to implement a single embodiment of the present invention. Accordingly, embodiments of the present invention are not limited to a single computing device 700, as would be appreciated by one with skill in the art, nor are they limited to a single type of implementation or configuration of the example computing device 700.

The computing device 700 can include a bus 710 that can be coupled to one or more of the following illustrative components, directly or indirectly: a memory 712, one or more processors 714, one or more presentation components 716, input/output ports 718, input/output components 720, and a power supply 724. One of skill in the art will appreciate that the bus 710 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 16 is merely illustrative of an exemplary computing device that can be used to implement one or more embodiments of the present invention, and in no way limits the invention.

The computing device 700 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 700.

The memory 712 can include computer-storage media in the form of volatile and/or nonvolatile memory. The memory 712 may be removable, non-removable, or any combination thereof. Exemplary hardware devices are devices such as hard drives, solid-state memory, optical-disc drives, and the like. The computing device 700 can include one or more processors that read data from components such as the memory 712, the various I/O components 716, etc. Presentation component(s) 716 present data indications to a user or other device. Exemplary presentation components include a display device, speaker, printing component, vibrating component, etc.

The I/O ports 718 can enable the computing device 700 to be logically coupled to other devices, such as I/O components 720. Some of the I/O components 720 can be built into the computing device 700. Examples of such I/O components 720 include a microphone, joystick, recording device, game pad, satellite dish, scanner, printer, wireless device, networking device, and the like.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A system for managing compliance with certified boundary conditions, the system comprising:
   a centralized management platform, comprising a processor, a pre-certification data map with de-identification rules, one or more databases and memory, configured to communicate data to and from a user device over a telecommunications network;
   an automapping module configured to map each field of a data set of the user device to standard field names, identify sensitive information and suggest one or more de-identification actions to anonymize values in each field in a manner compliant with regulations, and transfer to the centralized management platform a centrally stored data map;

a configuration tool configured to designate a sample record set size and modify the deidentification rules to be applied to fields in the data set of the user device when a user runs locally installed software to de-identify the data set;

a certification approval module configured to mark de-identification rules stored in the configuration tool as the certified rules and designate conditions or boundary ranges;

a monitoring data profile module configured to create baseline monitoring data files from the data set and comparator monitoring data files from a de-identified data set after the user runs the locally installed software to apply the certified rules to the data set; and a comparison module configured to compare attributes between comparator monitoring data files and baseline monitoring data files, and send an alert when any field deviates beyond designated conditions or boundary ranges.

2. The system of claim 1, further comprising a data converter module locally installed and configured to convert data in a database structure into a flat file format to create a flat file output for each table in a database of the data set, retaining field names and formats output to data files comprising the baseline monitoring data files, wherein the flat file output or outside sources serve as an input to the automapping module and serves as the baseline monitoring data files.

3. The system of claim 2, wherein the data converter module enables the user to designate one or more databases that the data converter module processes.

4. The system of claim 1, wherein centralized management platform comprises an invitation module that enables the user to invite a certifier to register to access files the user transmits to the centralized management platform, wherein registering, using a register module, further comprises:

registering one or more certifier and certifier software;

assigning one or more unique encryption keys and permissions to each of the one or more certifier and certifier software;

identifying parameters and requirements for certifier software;

generating configuration files for certifier and certifier software;

providing the unique encryption keys and configuration files to the certifier and certifier software at one or more certifier devices; and authenticating each certifier access using the permissions and the one or more unique encryption keys with the register module, wherein the transmitting is further based on authenticating using the permissions and the one or more unique encryption keys.

5. The system of claim 1, wherein the sensitive information in the data set comprises protected personally identifiable information (PII) or protected health information (PHI) and wherein a record set request derived from configuration tool input comprises a requested number of records based on the sample record set size.

6. The system of claim 1, wherein the sensitive information in the data set comprises one or more of social security numbers, credit card numbers, financial account information including financial account numbers, names including maiden names, birth dates, death dates, passport numbers, license numbers, certificate numbers, taxpayer identification numbers, patient identification numbers including medical record numbers, health plan beneficiary numbers, telephone numbers, fax numbers, personal identification numbers, title numbers, serial numbers, personal characteristic data including images, biometric identifying data, specific geographic identifiers, zip codes, personal addresses, street addresses, mailing addresses, email address information, uniform resource locator (URL), media access control (MAC) addresses, and internet protocol (IP) addresses.

7. The system of claim 1, wherein the automapping module is configured to identify and manage sensitive information in the data set of the user by parsing and processing each field in a flat file created from the data set, to identify a type of data contained in each field, a field name, and values in each field to map each field to a list of standard field names; analyzing a data format of the values in each field then matching, based on the data format of the values, elements of each field being analyzed against standard elements and assigning a suggested standard field name that is a match to map each field of a data set of the user to standard field names, and assigning a flag designating each field containing sensitive information values as personally identifiable information (PII) or protected health information (PHI), as well as assigning one or more suggested de-identification actions to anonymize the values in each field in a manner compliant with regulations, and automatically validating the type of data contained in each field.

8. The system of claim 1, wherein the automapping module outputs a data layout comprising assigned suggested standard field names, flags designating each field as personally identifiable information (PII) or protected health information (PHI), and assigned suggested de-identification actions for each field, and the automapping module enables the user to validate identified field types, modify, or add to the information in output data layouts, and to transfer a final data map from the automapping module to the centralized management platform to create a centrally stored data map.

9. The system of claim 1, wherein the automapping module assigns a standard field name associated with a specific data format and specific values comprising the specific data format.

10. The system of claim 1, wherein the automapping module assigns a standard field name comprising a name, a specific data format comprising text, and specific values in the specific data format comprising a list of actual names.

11. The system of claim 1, wherein the one or more suggested de-identification actions to anonymize the values comprises removing the values and sensitive information from each field of the data set to create a de-identified data set comprising data fields that are blank or nulled, and adding one or more unique encrypted tokens, each comprising a randomized character string, to each de-identified record of the de-identified data set, making each de-identified record of the data set unique to a particular individual but without the sensitive information and sensitive data values used to create each de-identified and tokenized record.

12. The system of claim 1, wherein the configuration tool is configured to designate a sample record set size for data to be received for analysis at the centralized management platform and wherein the configuration tool is configured to enable a certifier to modify the centrally stored data map to modify the de-identification rules to be applied to fields in the user's data set when the user runs locally installed software to de-identify the data set.

13. The system of claim 1, further comprising a statistical data profile module configured to process the de-identified data set created after the user runs locally installed software to de-identify the data set, creating output data tables to determine effectiveness of de-identification wherein each field is analyzed to create metrics for each field type, which are then transmitted to the centralized management platform.

14. The system of claim 13, wherein the statistical data profile module is configured to analyze each field and create metrics for each field type comprising one or more metrics selected from the group consisting of average, mode, median, sample size, fill rate, outliers, and combinations thereof, enabling the user to transmit the output data tables from the statistical data profile module to the centralized management platform, and wherein the statistical data profile module and the system are further configured to perform real-time calculations for metrics comprising k-anonymity or frequency indicating, based on a set level comprising a threshold for a certification standard for anonymity, whether the data meets certification requirements, wherein the metrics are included in the alert and in a reporting log stored in a database of the central management platform.

15. The system of claim 1, further comprising a sample data creation module configured to select a requested number of records from the de-identified data files to match the sample record set size designated by the configuration tool and transmit sample data created to the centralized management platform, wherein the sample data are ingested and stored by a data profile and a sample storage module configured to enable the certifier to retrieve files from for review and analysis.

16. The system of claim 1, wherein the certification approval module is configured to enable a certifier to mark rules stored in the configuration tool as the approved or certified rules and designate conditions or boundary ranges for individual fields in an approved data profile, and wherein the user runs the locally installed software to apply the certified rules from the certification approval module to de-identify the data set.

17. The system of claim 1, wherein the monitoring data profile module is configured to create a baseline monitoring data profile comprising baseline monitoring data files from the data set and a comparator monitoring data profile comprising comparator monitoring data files from a de-identified data set processed from a most current version of the data set after the user runs the locally installed software to apply the certified rules, then transmits the baseline monitoring data profile comprising the baseline monitoring data files from the data set and the comparator monitoring data profile comprising comparator monitoring data files to a central monitoring platform.

18. The system of claim 1, wherein the comparison module is further configured to store a baseline monitoring data profile and a comparator monitoring data profile within the central management platform to compare attributes of each field between comparator monitoring data files and baseline monitoring data files, to determine a degree of difference, then check the degree of difference in each field against the designated conditions or boundary ranges corresponding to each field set by the certifier using the certification approval module, and send an alert to the certifier and/or user when any field deviates by more than a set level that is beyond designated conditions or boundary ranges, recording a result in a reporting log stored in a database of the central management platform.

19. The system of claim 18, wherein the alert and the reporting log further comprise metrics and an identification of any fields or values that require modification to allow the set level comprising a threshold for a certification standard for anonymity, to be met or surpassed.

20. The system of claim 1, wherein
the system comprises a plurality of user devices, the centralized management platform comprises a plurality of processors, one or more pre-certification data maps with de-identification rules, one or more databases and memory, configured to communicate data to and from the plurality of user devices over a telecommunications network;
one or more automapping modules are configured to map each field of one or more data sets of the plurality of user devices to standard field names, identify sensitive information and suggest de-identification actions to anonymize values in each field in a manner compliant with regulations, and transfer to the centralized management platform one or more centrally stored data maps;
the configuration tool is configured to designate a sample record set size and modify the de-identification rules to be applied to fields in the one or more data sets of the plurality of user devices when one or more users run locally installed software to de-identify the one or more data sets; and
one or more monitoring data profile modules are configured to create baseline monitoring data files from the one or more data sets and comparator monitoring data files from one or more de-identified data sets after the one or more users run the locally installed software to apply the certified rules to the one or more data sets.

21. A method for managing compliance with certified boundary conditions, the method comprising:
receiving, a at centralized management platform comprising a processor, a pre-certification data map with de-identification rules, one or more databases, and memory, a data set from a user device configured to communicate over a telecommunications network;
analyzing, using an automapping module, values in each field of the data set, mapping each field to standard field names, identifying sensitive information and suggesting de-identification actions compliant with regulations, then transferring a centrally stored data map to the centralized management platform;
modifying, using a configuration tool, the de-identification rules to be applied to fields in the data set of the user when the user runs locally installed software to de-identify the data set;
determining, using a statistical data profile module, effectiveness of de-identification and creating metrics for each field type then transmitting output data tables to the centralized management platform;
marking, using a certification approval module, rules stored in the configuration tool as the approved or certified rules, and designating conditions or boundary ranges;
creating, using a monitoring data profile module, a baseline monitoring data profile from the data set and a comparator monitoring data profile from a de-identified data set after the user runs the locally installed software to apply the certified rules; and
comparing, using a comparison module, attributes between comparator monitoring data files and baseline monitoring data files, and sending an alert when any field deviates beyond designated conditions or boundary ranges.

* * * * *